United States Patent
Exline

[11] Patent Number: 5,843,040
[45] Date of Patent: Dec. 1, 1998

[54] SURGICAL SLEEVE OR CANNULA WITH ROTATING REDUCER

[75] Inventor: Donald D. Exline, Carrollton, Tex.

[73] Assignee: Dexide, Inc., Fort Worth, Tex.

[21] Appl. No.: 851,670

[22] Filed: May 6, 1997

[51] Int. Cl.$^6$ .................................................. A61M 5/178
[52] U.S. Cl. ............................................................ 604/164
[58] Field of Search ................................... 604/164, 165, 604/167, 256, 248, 247

[56] References Cited

U.S. PATENT DOCUMENTS

| | | | |
|---|---|---|---|
| 4,112,932 | 9/1978 | Chiulli | 128/3 |
| 4,822,344 | 4/1989 | O'Boyle | 604/248 |
| 5,112,321 | 5/1992 | Hiltebrandt | 604/167 X |
| 5,122,122 | 6/1992 | Allgood | 604/167 X |
| 5,350,362 | 9/1994 | Stouder, Jr. | 604/167 |
| 5,395,342 | 3/1995 | Yoon | 604/164 X |
| 5,437,626 | 8/1995 | Cohen et al. | 604/167 X |
| 5,439,455 | 8/1995 | Kieturakis et al. | 604/167 X |
| 5,512,053 | 4/1996 | Pearson et al. | 604/167 |
| 5,531,758 | 7/1996 | Uschold et al. | 604/167 X |
| 5,611,792 | 3/1997 | Gustafsson | 604/167 X |
| 5,676,657 | 10/1997 | Yoon | 604/167 |

*Primary Examiner*—Manuel Mendez

[57] ABSTRACT

A surgical sleeve that includes a housing has an opening through which surgical instruments are introduced into the surgical sleeve. A sleeve portion extends from the housing and has an inner diameter coaxial with the opening in the housing. A reducer assembly is removably secured to the housing and includes a rigid seal disc for rotation in a plane transverse to the sleeve portion. A resilient, laminar seal layer is generally coextensive with the seal disc and is disposed between the disc and the housing to sealingly engage a portion of the housing. A plurality of apertures are formed in the seal disc and seal layer and have varying diameters to define seals that are selectively movable, by rotation of the seal disc, over the opening in the housing to seal against exteriors of instruments disposed in the sleeve.

18 Claims, 2 Drawing Sheets

SURGICAL SLEEVE OR CANNULA WITH ROTATING REDUCER

BACKGROUND OF THE INVENTION

1. Field of the Invention

The present invention relates generally to surgical instruments, and more particularly to cannulas or sleeves employed in endoscopic surgery.

2. Background Information

Surgical sleeves or cannulas are conventionally used in endoscopic or laparoscopic surgery to facilitate passage of surgical instruments such as endoscopes, clip appliers, and the like into a body cavity, usually the abdominal cavity. The sleeve is inserted through an incision made in the abdominal wall and into the body cavity, where it remains until the surgery is concluded. Various surgical instruments then are passed through the sleeve and into the body cavity to accomplish this surgical procedures. Often, the body cavity is insufflated with an inert gas, such $CO_2$, to lift the abdominal wall to facilitate viewing of the interior of the body cavity with the endoscope.

A recent improvement to these surgical sleeves is to provide the sleeve with an expandable member that is selectively expanded within the body cavity to prevent inadvertent full or partial withdrawal of the sleeve from the body cavity. Such surgical sleeves are disclosed in commonly assigned U.S. Pat. Nos. 5,122,122 and 5,217,451. The sleeves disclosed in those patents employ an expandable member in the form of an expandable hinge formed by a plurality of longitudinal slits made in the outer sleeve. Relative movement between inner and outer sleeves causes the expandable hinge structure to expand radially, wherein the sleeve resists withdrawal from the body cavity.

Surgical sleeves such as those disclosed in U.S. Pat. Nos. 5,122,122 and 5,217,451 are used with surgical instruments in varying diameter. Typically, the sleeve is chosen to have an interior diameter large enough to accommodate the largest diameter instrument to be used with the sleeve. The sleeves are provided with seals that obstruct the inner diameter of the sleeve to prevent escape of insufflation gas from the body cavity, whether an instrument is present in the sleeve or not. Such seals typically include a lip seal for the sealing the interior passage of the sleeve when an instrument is not present in the sleeve, and an outer-diameter (O.D.) seal to seal against the outer diameter of an instrument present in the sleeve.

By necessity, the O.D. seal in a 12 mm sleeve can only seal against instruments having outer diameters between 10 and 11 mm, but not against instruments much smaller than 10 mm in diameter. If a smaller diameter instrument is to be used with a sleeve, an auxiliary O.D. seal must be employed. These auxiliary O.D. seals are commonly known as "reducers," and as relatively small and separate parts, are clumsy in operation and represent one more item for operating room personnel to account for during surgical procedures.

One solution to the foregoing shortcomings is disclosed in commonly assigned U.S. Pat. No. 5,512,053, Apr. 30, 1996 to Pearson et al. in which a transversely sliding reducer is provided for a sleeve or cannula. An interesting variation on the reducer theme is shown in U.S. Pat. No. 4,112,932, to Chiulli, which discloses a rotatable "turret" having seals of varying diameter. The turret is rotated to align one of the seals with the sleeve portion of the cannula. The Chiulli mechanism is useful, but the sealing arrangement is difficult to manufacture and may have seal reliability problems as a result.

A need exists for a surgical sleeve provided with an integral reducer capable of sealing against surgical instruments having a variety of outer diameters and having improved means for aligning seals of different diameters with the sleeve portion of the cannula.

SUMMARY OF THE INVENTION

It is a general object of the present invention to provide an improved surgical sleeve or cannula for use in endoscopic surgical procedures. This and other objects of the present invention are achieved by providing a surgical sleeve that includes a housing having an opening through which surgical instruments are introduced into the surgical sleeve. A sleeve portion extends from the housing and has an inner diameter coaxial with the opening in the housing. A reducer assembly is removably secured to the housing and includes a rigid seal disc for rotation in a plane transverse to the sleeve portion. A resilient, laminar seal layer is generally coextensive with the seal disc and is disposed between the disc and the housing to sealingly engage a portion of the housing. A plurality of apertures are formed in the seal disc and seal layer and have varying diameters to define seals that are selectively movable, by rotation of the seal disc, over the opening in the housing to seal against exteriors of instruments disposed in the sleeve.

According to the preferred embodiment of the present invention, the rotatable reducer assembly is removable from the housing to provide quick access to the full-diameter opening in the housing.

According to the preferred embodiment of the present invention, the sleeve portion of the surgical sleeve includes an expandable member generally opposite the housing. The expandable member is selectively radially expandable within the body cavity to resist withdrawal of the surgical sleeve.

According to the preferred embodiment of the present invention, the reducer assembly is provided with a visual indicia of the diameter of the seal that is aligned with the sleeve portion.

According to the preferred embodiment of the present invention, a seal disc cap is disposed over the seal disc and is carried by the housing. A viewing aperture is formed in the seal disc cap for operator viewing of the visual indicia of seal diameter on the seal disc.

DESCRIPTION OF THE PREFERRED EMBODIMENT

Figure 1:
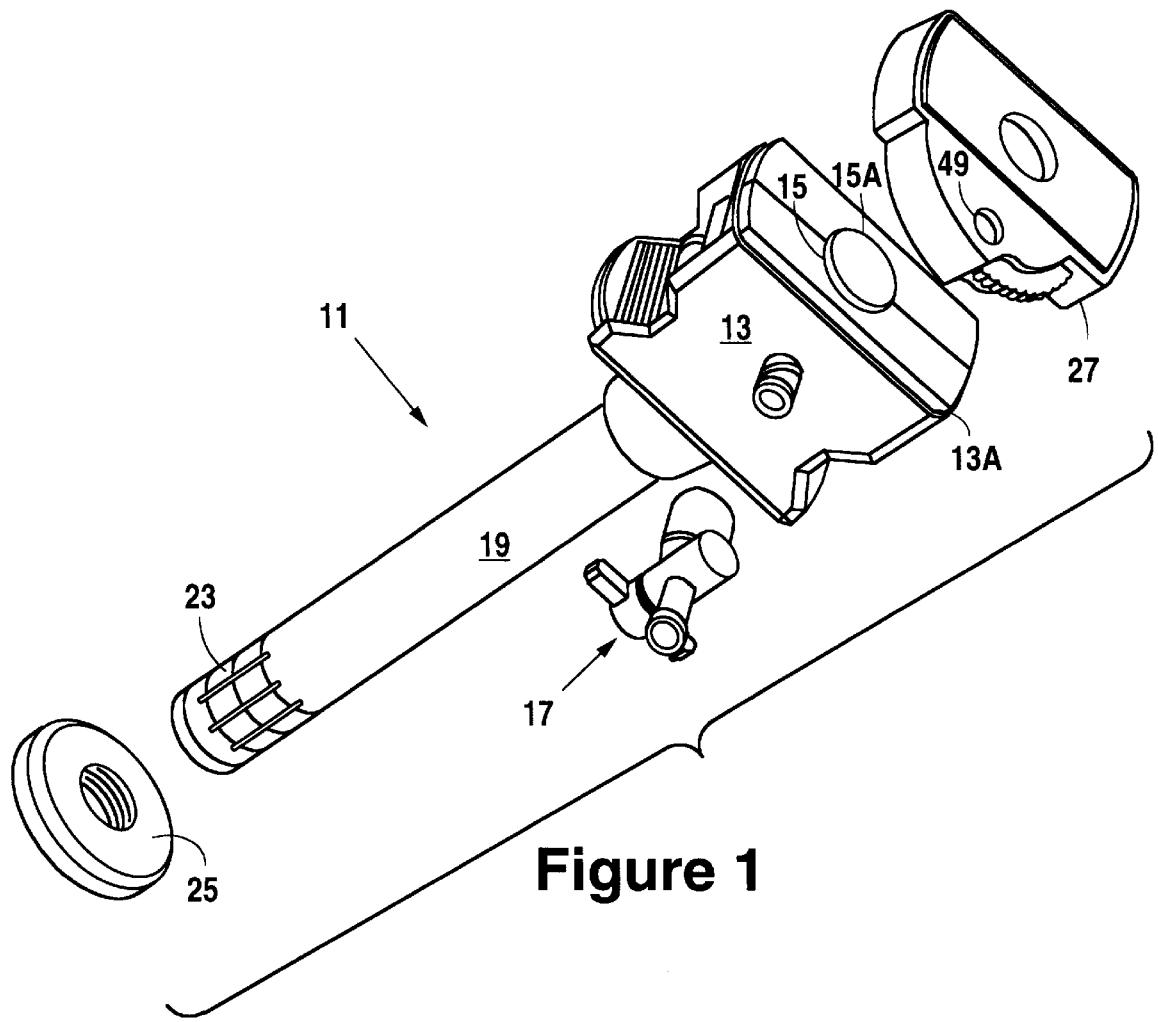
FIG. 1 is an exploded perspective view of the surgical sleeve according to the present invention.

Referring now to FIG. 1, a surgical sleeve or cannula 11 according to the present invention is illustrated. Surgical sleeve 11 comprises a housing 13, which is provided with an opening 15 at its upper end for introduction of surgical instruments (not shown) into sleeve 11. A lip or protrusion 15A surrounds opening 15 and projects beyond the upper surface of housing 13. Housing 13 is formed of ABS plastic and is further provided with a polycarbonate Luer fitting and stopcock 17 for attachment of a fluid pressure source (not shown) to supply insufflation gas through sleeve 11 to the body cavity (not shown) in which sleeve 11 is inserted.

A sleeve portion 19 (comprising inner and outer sleeves) extends from housing 13 and terminates in an expandable member 21. A conventional lip seal, such as that disclosed in U.S. Pat. No. 5,512,053 is disposed in housing between opening 15 and sleeve portion 21 to provide a seal against fluid leakage through sleeve 11 when no instrument is present. Manipulation of a trigger 21 carried by housing 13 causes radially outward expansion of expandable member 23 on sleeve portion 19 to resist the withdrawal of sleeve from the body cavity in which it is inserted. A disc-like Santoprene™ elastomer stop member 25 is slidably carried on the exterior of sleeve portion to be moved against the exterior of the abdomen (not shown) to cooperate with expandable member 23 in immobilizing and sealing sleeve in the body cavity. In these aspects of the invention, sleeve 11 is constructed in accordance with commonly assigned U.S. Pat. No. 5,512,053, which is incorporated by reference.

A rotating reducer assembly 27 is secured to the upper-end of housing 13 generally opposite the end of housing from which sleeve portion 21 extends. Reducer assembly 27 is removably secured to housing 13 by a snap-together arrangement including a groove 13A formed on each side of housing 13, which cooperates with an interior shoulder (not shown) on reducer assembly 27. Thus, reducer assembly is easily removable from housing 13 to provide quick and easy access (even with an instrument disposed in sleeve 11) to full-diameter opening 15 to withdraw large pieces of tissue or the like that cannot easily pass through the O.D. seals provided by reducer assembly 22.

Figure 2:
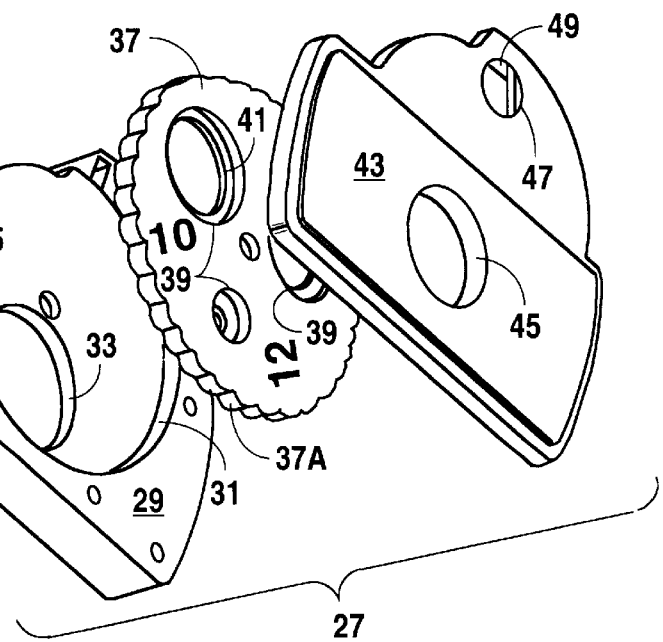
FIG. 2 is an exploded perspective view of the reducer assembly of the surgical sleeve of FIG. 1.

FIG. 2 is an exploded perspective view of rotating reducer assembly 27 according to the present invention. Reducer assembly 27 comprises a reducer body 29, which is provided with a generally circular recess 31 and an aperture 33 for alignment with opening 15 in housing 13. A pawl or lever 35 is integrally molded into reducer body 29 about the circumference of circular recess 31.

Pawl 35 engages lugs 37A on the periphery or outer diameter of a rigid seal disc 37, which is disposed for rotation in circular recess 31 of reducer body 29, to provide a detent to stop rotation of seal disc 37 when a seal aperture is aligned over opening 15. Seal disc 37 is formed of a Verton™ glass-filled polyprophylene and is provided with a plurality of, preferably three, apertures 39. Apertures 39 and corresponding apertures in a resilient seal layer 41 cooperate to define outer-diameter (O.D.) seals for sealing against fluid loss around the outer diameter of a surgical instrument inserted or disposed within surgical sleeve 11.

A seal disc cap 43 is disposed over seal disc 37 and confines seal disc 37 within circular recess 31 of reducer body 29 such that seal disc 37 is rotatable in a plane generally transverse to the longitudinal axis of sleeve portion 21. Seal disc cap 43 is provided with an aperture 45 that is coaxial with aperture 33 in reducer body 29, opening 15 in housing 13, and the inner diameter of sleeve portion 21. A portion of seal cap 43 extends over seal disc 37 and is provided with a viewing aperture for viewing the visual indicia ("10" and "12") provided on seal disc 37 that are indicative of the seal diameter aligned over opening 15 of housing 13.

Figure 3:
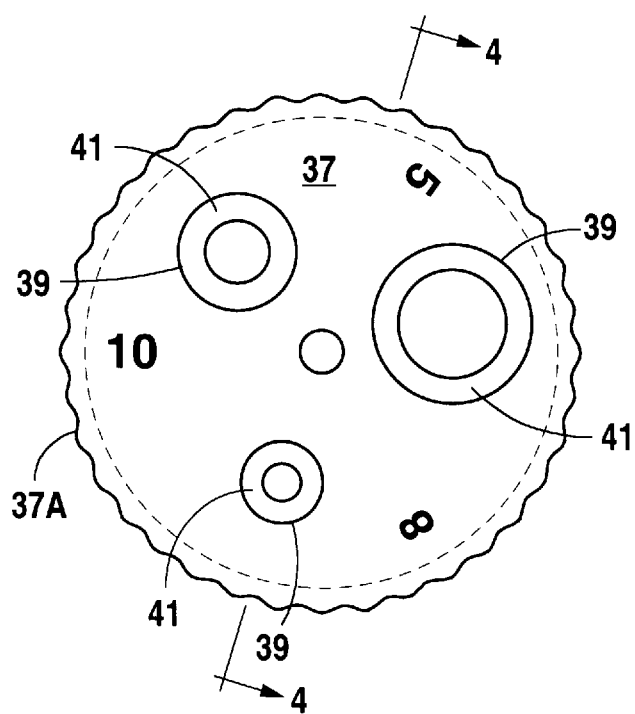
FIG. 3 is a plan view of the seal disc of the reducer assembly of FIG. 2.
Figure 4:
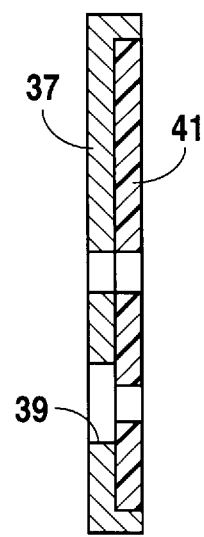
FIG. 4 is a section view of the seal disc of FIG. 3, taken along section line 4—4 of FIG. 3.

FIGS. 3 and 4 are enlarged plan and section views, respectively, of seal disc 37 according to the preferred embodiment of the invention. Seal disc 37 is provided with three equally angularly spaced apertures 39. Visual indicia ("10," "8," and "5") of the seal diameter are imprinted on disc 37 at locations (generally opposite the corresponding seal or aperture) where they will be aligned with and viewed through aperture 49 when the corresponding seal is aligned with opening 15.

As better seen in FIG. 4, a resilient, laminar seal layer 41, formed of Santoprene™ polyprophylene elastomer material, is secured to the underside of disc 37. Seal layer 41 is generally coextensive with the seal disc 37 and is provided with three apertures corresponding to apertures 39 in seal disc. The apertures in seal disc 37 and seal layer 41 are a variety of diameters designed to seal against fluid loss around the exterior of surgical instruments of varying diameter inserted or disposed in sleeve 11. For example, seal disc 37 in FIG. 3 has seals or apertures designed to seal against instruments having 10 mm, 8 mm, and 5 mm nominal outer diameters. The corresponding apertures in elastomer seal layer 41 are approximately 7.7 mm, 4.7 mm, and 2.7 mm in diameter respectively. Seal disc 37 in FIG. 2 has apertures as seals for instruments having 12 mm, 10 mm, and 5 mm (not shown) nominal outer diameters. The corresponding apertures in elastomer seal layer 41 are approximately 10.4 mm, 7.7 mm, and 2.7 mm in diameter respectively. Upon assembly, seal layer compressed by protrusion 15A from housing 13, thus providing a positive fluid seal between seal disc 37 and housing 13.

In operation, sleeve 11 is inserted into a body cavity, usually with the assistance of a sharpened trocar disposed in sleeve 11. Trigger 21 is selectively actuated to expand expandable member 23 to resist withdrawal of sleeve 11 from body cavity. The body cavity may be insufflated with gas provided through Luer fitting 17 and sleeve 11 to provide easier viewing of the cavity.

A surgical instrument of a given diameter is inserted through sleeve 11 and into body cavity. The instrument breaks the seal against loss of insufflation gas provided by the internal lip seal, but the outer-diameter seal of reducer assembly 27 prevents loss of gas around the instrument. If an instrument of different diameter is inserted, a different O.D. seal of appropriate diameter is selected by rotation of seal disc 37. Pawl 35 provides a detent or stop when the seal is properly aligned over opening 15 of housing 13. If it becomes necessary to withdraw a large object or piece of tissue through sleeve 11, reducer assembly 27 may be easily removed from housing 13, the instrument and object or tissue withdrawn, and reducer assembly 27 replaced.

The invention has been described with reference to a preferred embodiment thereof. It is thus not limited, but is susceptible to variation and modification without departing from the scope and spirit of the invention.

I claim:

1. A surgical sleeve for the introduction of surgical instruments into a body cavity, the surgical sleeve comprising:
    (a) a housing having an opening enabling surgical instruments to be introduced into the sleeve;
    (b) a sleeve portion extending from the housing coaxially with the opening in the housing; and
    (c) a reducer assembly removably secured to the housing and further comprising:
        (i) a rigid seal disc mounted for rotation in a plane transverse to the sleeve portion;
        (ii) a resilient, laminar seal layer generally coextensive with the seal disc and disposed between the seal disc and the housing and sealingly engaging a portion of the housing; and (iii) a plurality of apertures formed in the seal disc and seal layer, the apertures having varying diameters to define seals that are selectively movable, by rotation of the seal disc, over the opening in the housing to seal against exteriors of instruments disposed in the sleeve.

2. The surgical sleeve according to claim 1 further comprising:

an expandable member carried by the sleeve portion generally opposite the housing, the expandable member selectively radially expandable within the body cavity to resist withdrawal of the surgical sleeve.

3. The surgical sleeve according to claim 1 further comprising:

a seal disc cap disposed over a cooperative seal disc carried by the housing;

a viewing aperture formed in the seal disc cap for viewing a visual indicia of seal diameter of the seal disc disposed over the opening in the housing.

4. The surgical sleeve according to claim 1 wherein the reducer assembly is provided with visual indicia of the seal diameter aligned with the sleeve portion.

5. A surgical sleeve for the introduction of surgical instruments into a body cavity, the surgical sleeve comprising:

a housing having an opening enabling surgical instruments to be introduced into the sleeve;

a sleeve portion extending from the housing coaxially with the opening in the housing; and a reducer assembly secured to the housing, including:
a rigid seal disc mounted for rotation in a plane transverse to the sleeve portion;
a resilient, laminar seal layer generally coextensive with the seal disc and disposed between the seal disc and the housing and sealingly engaging in a portion of the housing; and
a plurality of apertures formed in the seal disc and seal layer, the apertures having varying diameters to define seals that are selectively movable, by rotation of the seal disc, over the opening in the housing to seal against exteriors of instruments disposed in the sleeve.

6. The surgical sleeve according to claim 5 further comprising:

an expandable member carried by the sleeve portion generally opposite the housing, the expandable member selectively radially expandable within the body cavity to resist withdrawal of the surgical sleeve.

7. The surgical sleeve according to claim 5 further comprising:

a seal disc cap disposed over a cooperative seal disc carried by the housing;

a viewing aperture formed in the seal disc cap for viewing a visual indicia of seal diameter of the seal disc that is disposed over the opening in the housing.

8. The surgical sleeve according to claim 5 wherein the reducer assembly is provided with visual indicia of the seal diameter aligned with the sleeve portion.

9. The surgical sleeve according to claim 5 wherein the reducer assembly is removable from the housing for access to the opening in the housing.

10. A surgical sleeve for the introduction of surgical instruments into a body cavity, the surgical sleeve comprising:

an elongate sleeve portion having an inner diameter for the passage of surgical instruments through the surgical sleeve;

a housing secured to one end of the sleeve portion, the housing having an opening aligned with the inner diameter, the opening including a protrusion above the housing; and a reducer assembly secured to the housing opposite the sleeve portion, including:
a rigid seal disc;
a resilient, laminar seal layer generally coextensive with the seal disc and disposed, between the seal disc and the housing and sealingly engaging the protrusion on the housing; and
a plurality of apertures formed in the seal disc and seal layer, the apertures having varying diameters and defining seals that are selectively movable, by rotation of the seal disc, over the opening in the housing to seal against exteriors of instruments disposed in the sleeve; and
a seal disc cap securing the seal disc to the housing, the seal disc cap including a pivot point to enable the seal disc rotation in a plane generally transverse to the sleeve portion.

11. The surgical sleeve according to claim 10 further comprising:

an expandable member carried on the sleeve portion generally opposite the housing, the expandable member selectively radially expandable within the body cavity to resist withdrawal of the surgical sleeve.

12. The surgical sleeve according to claim 10 further comprising:

a viewing aperture formed in the seal disc cap for viewing a visual indicia of seal diameter on the seal disc.

13. The surgical sleeve according to claim 10 wherein the reducer assembly is removable from the housing for access to the opening in the housing.

14. A surgical sleeve for the introduction of surgical instruments into a body cavity, the surgical sleeve comprising:

an elongate sleeve portion having an inner diameter for the passage of surgical instruments through the surgical sleeve;

a housing secured to one end of the sleeve portion, the housing having an opening aligned with the inner diameter of the sleeve portion;

an expandable member formed on the sleeve portion generally opposite the housing and selectively radially expandable within the body cavity to resist withdrawal of the surgical sleeve from the body cavity; and a reducer assembly mounted to the housing and including:
a rigid seal disc mounted for rotation on the housing transverse to the sleeve portion;
a resilient, laminar seal layer generally coextensive with the seal disc and disposed between the seal disc and the housing and sealingly engaging a portion of the housing;
a plurality of seal apertures formed in the seal disc and seal layer, the seal apertures having varying diameters and defining seals that are selectively movable, by rotation of the seal disc, over the opening in the housing to seal against exteriors of instruments disposed in the sleeve.

15. The seal assembly according to claim 14 further comprising:

a seal disc cap securing the seal disc to the housing, the seal disc cap including a pivot point about which the seal disc rotates.

16. The surgical sleeve according to claim 14 wherein the expandable member comprises:
   a plurality of longitudinally extending slits in the sleeve portion, wherein compression of the expandable member causes radial expansion of material between the slits.

17. The surgical sleeve according to claim 14 further comprising:

a viewing aperture formed in the seal disc cap for viewing a visual indicia of seal diameter on the seal disc.

18. The surgical sleeve according to claim 14 wherein the reducer assembly is removable from the housing for access to the opening in the housing.

* * * * *